United States Patent [19]

Braden et al.

[11] Patent Number: 5,718,924
[45] Date of Patent: Feb. 17, 1998

[54] FLUORIDE RELEASING BIOMATERIALS

[75] Inventors: Michael Braden, Hertz; Mangala Prakesh Patel, London; Gavin John Pearson, Ashampstead, all of United Kingdom

[73] Assignee: Eastman Dental Institute, London, England

[21] Appl. No.: 589,010

[22] Filed: Jan. 19, 1996

[30] Foreign Application Priority Data

Jan. 19, 1995 [GB] United Kingdom .................. 9501183

[51] Int. Cl.$^6$ ................... A61K 6/02; A61K 6/08
[52] U.S. Cl. ............ 424/673; 424/675; 424/676; 523/109; 523/115; 523/116; 523/118
[58] Field of Search ................. 424/673, 675, 424/676; 523/109, 115, 116, 118

[56] References Cited

U.S. PATENT DOCUMENTS

| | | | |
|---|---|---|---|
| 3,625,916 | 12/1971 | Newman | 260/41 |
| 4,001,483 | 1/1977 | Lee, Jr. et al. | 526/270 |
| 4,264,489 | 4/1981 | Ibsen et al. | 525/284 |
| 4,282,140 | 8/1981 | Bousquet et al. | 260/42.52 |
| 4,337,186 | 6/1982 | Crisp | 525/362 |
| 4,372,836 | 2/1983 | Schmitt et al. | 204/159.23 |
| 4,791,150 | 12/1988 | Braden et al. | 523/117 |
| 5,034,433 | 7/1991 | Cohen et al. | 523/400 |
| 5,171,763 | 12/1992 | Ohno et al. | 523/116 |
| 5,204,398 | 4/1993 | Cohen et al. | 524/403 |

FOREIGN PATENT DOCUMENTS

| | | |
|---|---|---|
| 0 356 868 | 3/1990 | European Pat. Off. . |
| 0 449 399 | 10/1991 | European Pat. Off. . |
| 0 544 890 | 8/1993 | European Pat. Off. . |
| 2 077 281B | 12/1981 | United Kingdom . |
| 2 107 341B | 4/1983 | United Kingdom . |
| 2 219 303B | 12/1989 | United Kingdom . |
| WO 81/02022 | 7/1981 | WIPO . |
| WO 93/09819 | 5/1993 | WIPO . |

OTHER PUBLICATIONS

Chemical Abstracts, vol.3, No. 6, Aug. 12, 1985, Columbus, Ohio, US.

Primary Examiner—Frederick Krass
Attorney, Agent, or Firm—Wolf, Greenfield & Sacks, P.C.

[57] ABSTRACT

A fluoride releasing dental composition comprising a polymer, a monomer and a metal fluoride. The polymer may be an acrylate polymer, a methacrylate polymer or a copolymer thereof. The monomer may be a monomeric heterocyclic acrylic ester, a monomeric heterocyclic methacrylic ester, a $C_3$–$C_{16}$ alkyl acrylic ester or a $C_3$–$C_{16}$ methacrylic ester. The metal fluoride is a nontoxic, biologically acceptable metal fluoride. In certain embodiments, the metal fluoride is sodium fluoride. The metal fluoride may comprise from approximately 0.1% to approximately 2% of the composition by weight.

11 Claims, 4 Drawing Sheets

PEM/THFM CONTAINING 1% NaF IN WATER, ARTIFICIAL SALIVA AND PHOSPHATE BUFFERED SOLUTION

FLUORIDE RELEASING BIOMATERIALS

BACKGROUND OF THE INVENTION

1. Field of the Invention

The present invention relates generally to fluoride releasing biomaterials, and more specifically to such materials intended for use in dental applications including coatings, fillings, endodontic materials and orthodontic cements.

2. Discussion of the Related Art

The use of physiologically acceptable polymeric materials is well known in the preparation of biomedical appliances such as hearing aids, artificial eyes and dentures. Such materials are also used as bone cements and the like.

GB-A-2107341 discloses low shrinkage monomer/ copolymer compositions prepared by mixing a ligand component containing tetrahydrofurfuryl methacrylate with a solid component. The solid component is polyethylmethacrylate or a copolymer of ethyl methacrylate and methyl methacrylate, propyl methacrylate or butyl methacrylate. The linear shrinkage of the polymeric material is preferably between 0.2% and 1.0%. The materials are stated to be of particular use for hearing aids, dental bridges, dental crowns, dentures, contact lenses, artificial eyes and other biomedical applications.

GB-A-2219303 discloses a two-phase cement mixture for orthopedic use comprising a solid phase which is polymethyl methacrylate and a liquid phase which is monomethyl methacrylate. The solid phase may have certain fluoride materials added thereto to make fluoride ions available to the bone.

WO93/09819 discloses a monomer/polymer mixture for use in the preparation of a curable composition for introduction to a site requiring tissue repair in a human or animal body. The monomer component is an acrylate or methacrylate containing a heterocyclic ring, and the polymer component is a polyacraylate, polymethacrylate or an acrylate-methacrylate copolymer.

EP-A-0554890 discloses a dental composite composition which includes polyakenoic acid, a filler which provides elutable cations which are reactive with the polyakenoic acid, fluoride ion, water, a polymerizable monomer and/or prepolymer composition, an unsaturated organic acid containing one or more polymerizable groups and a catalyst system for polymerization. The compositions may be used as cement, liner, base, restorative, pit and fissure sealants, and/or core build up materials. The glass filler material is preferably a fluoralumino silicate glass powder.

EP-A-0449399 discloses polymerizable dental materials comprising at least one polymerizable monomer or prepolymer, a catalyst and at least one inorganic filler. The inorganic filler is a glass powder containing 40 to 75 wt % CaO, 5 to 30 wt %, $B_2O_3$ and 5 to 35 wt % $SiO_2$. The material may optionally contain other inorganic fillers such as $YbF_3$ to render the material radioopaque, but the $YbF_3$ is substantially water insoluble.

The only current fluoride releasing materials are glass ionomer (polyalkenoate) cements, such as disclosed in GB-A-2077281 and U.S. Pat. No. 4,337,186. These materials both release fluoride to inhibit caries and are adhesive to calcified tissue. However, they have relatively low strength and solubility in oral fluids. Therefore, their use is limited.

Room temperature polyermising (methyl methacrylate) systems cannot be used directly in the mouth because of mucosal irritation. Also, they have well documented disadvantages as orthopedic bone cements. These disadvantages include high exotherm, hypotensive effects during surgery and brittleness. Furthermore, the low water uptake of these materials severely restricts their fluoride release. The dimethacrylates used in restorative dental materials also have low water uptake. In addition, these dimethacrylates are highly cross-linked. Hence, they have severely restricted fluoride release.

SUMMARY OF THE INVENTION

In one illustrative embodiment, the present invention provides a fluoride releasing dental composition which comprises a polymer, a monomer and a metal fluoride. The metal fluoride is present in an amount sufficient to release at least approximately 1 part per million of fluoride from the dental composition to distilled water after the dental composition has been stored in the distilled water for 18 weeks.

In another illustrative embodiment, the present invention provides a fluoride releasing dental composition comprising a polymer, a monomer and a metal fluoride. The dental composition comprises from approximately 0.1% to approximately 2% metal fluoride by weight.

In a further illustrative embodiment, the present invention provides a fluoride releasing dental composition comprising a polymer, a monomer and a metal fluoride. The polymer may be an acrylate polymer, a methacrylate polymer, an acrylate copolymer, a methacrylate copolymer or a mixture thereof. The monomer may be a monomeric heterocyclic acrylic ester, a monomeric heterocyclic methyl acrylic ester, a $C_3$–$C_{16}$ methacrylic ester, a $C_3$—$C_{16}$ alkyl acrylic ester or a mixture thereof.

Metal fluorides appropriate for use in the present invention are preferably nontoxic and biologically acceptable.

BRIEF DESCRIPTION OF THE DRAWINGS

The present invention will be more clearly appreciated from the following detailed description when taken in conjunction with the accompanying drawings, in which.

DETAILED DESCRIPTION OF THE INVENTION

Figure 1:
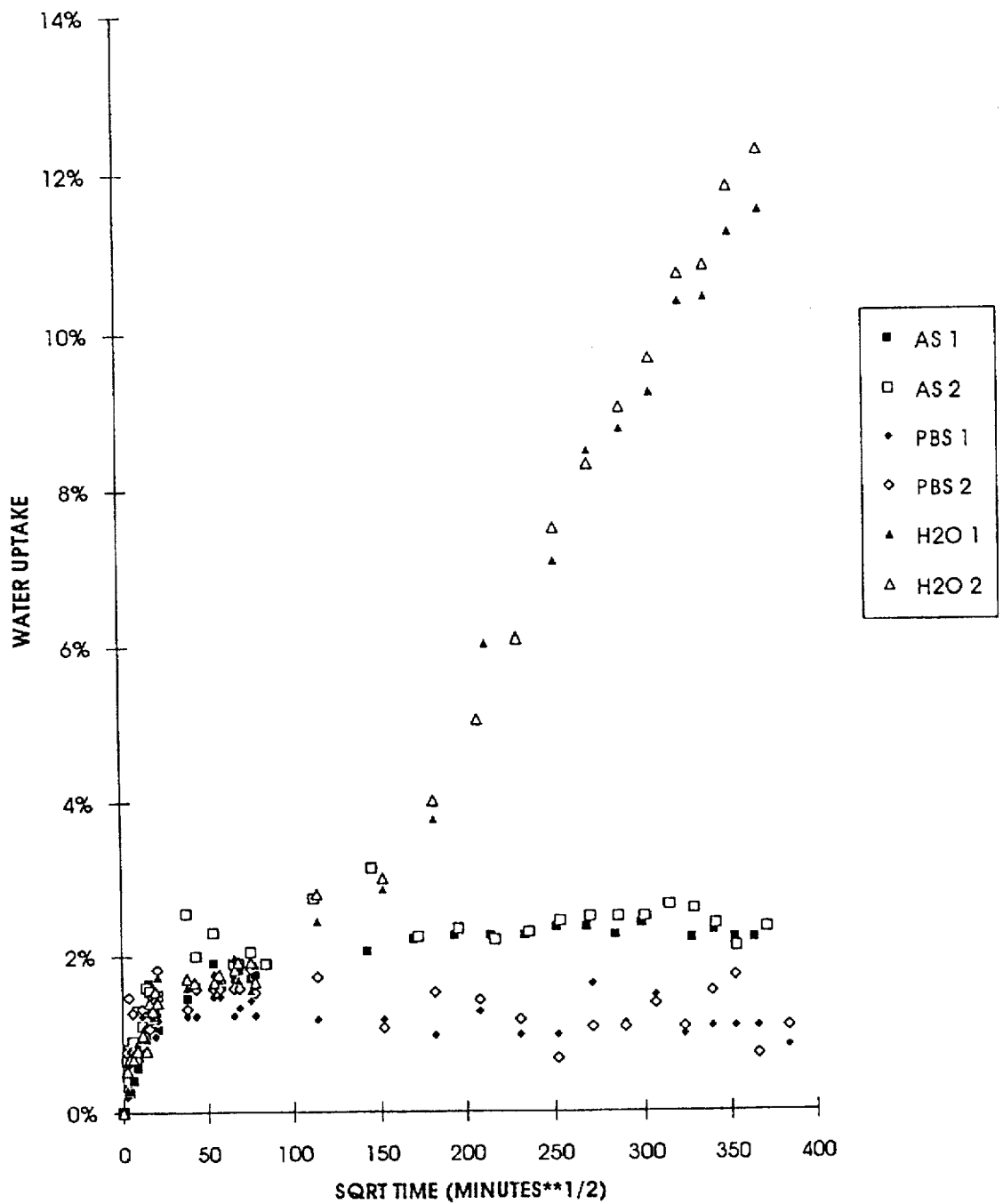
FIG. 1 illustrates the water uptake of the composition of Example 1 containing 0% w/w sodium fluoride in various media.

The heterocyclic monomer component of the compositions of the present invention preferably has the general formula

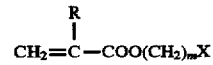

where R is a hydrogen atom or a methyl group, m is 0, 1 or 2 and X is a 3 to 6 membered heterocyclic ring. The group X is preferably a 3 to 6 membered ring containing oxygen, more preferably a tetrahydrofurfuryl group. The alkyl methacrylic ester which may be used as the monomer component is preferably a $C_4$ alkyl ester, more preferably an n-butyl ester for the production of rigid polymeric materials. When n is greater than 4, the methacrylate materials are compliant and less reactive.

The monomer may be admixed with one or more other monomers to control hydrophilicity. For example, hydroxyethyl methacrylate may be used to increase hydrophilicity, or isobornyl methacrylate may be used to decrease hydrophilicity. The polymer component is preferably a methacrylate polymer, more preferably poly(ethylmethacrylate). Other polymers, such as poly(methylmethacrylate), poly(hydroxyethylmethacrylate), poly(tetrahydrofurfurylmethacrylate) and copolymers thereof, may also be employed. In certain embodiments, the copolymer component may be selected to control hydrophilicity.

The composition is preferably in the form of a mixture of finely divided solid polymer. In a preferred embodiment, the composition is prepared by suspension polymerization in liquid monomer. The composition may initially include, or have added to it at the point of use, suitable activators for curing. Such activators include free radical catalysts (e.g., peroxide/amine initiator systems). Alternatively, photoinitiators may be used (e.g., camphor quinone/tertiary amine systems which are well known in the art). Additional additives such as stabilizers, fillers and x-ray opacifying agents may also be included if desired. These include, for example, quinone type inhibitors in the monomer, and/or inorganic fillers to increase hardness and reduce polymerization shrinkage. In particular, hydroxyapatite may be used for this purpose and to improve biocompatability.

The ratio of the monomer to the polymer component in the compositions of the present invention may vary depending upon the cure time and the initially desired consistency of the composition. Preferably, the ratio of polymer to monomer is 1:1 to 3:1 by weight, more preferably 1.25:1 to 1.75:1. Curing of the composition preferably occurs at body temperature, and curing is generally effected over a period of time of 5 to 20 minutes. In a preferred embodiment, curing preferably is effected over a time period of 10 to 15 minutes.

Metal fluorides appropriate for use in the present invention are preferably nontoxic and biologically acceptable. Such metal fluorides are known to those skilled in the art and include, for example, sodium fluoride, potassium fluoride, tin fluoride, calcium fluoride, zinc fluoride, bismuth fluoride or a mixture thereof. Preferably, the metal fluoride comprises sodium fluoride. In certain embodiments, the metal fluoride is from approximately 0.1% to approximately 2% of the composition by weight. In a preferred embodiment, the metal fluoride is from approximately 0.5% to approximately 1.0% of the composition by weight. Typically, the metal fluoride is in finely divided form and admixed with the polymer component.

The compositions of the present invention may be used as dental preventative or dental restoration materials. For example they may be used as dental coating materials, filling materials, endodontic materials, orthodontic cements, or the like.

It is believed that the ability of such cured compositions to release fluoride results from their ability to absorb water to an extent which enables the metal fluoride present in the compositions to diffuse into the tooth tissue.

The following examples of certain embodiments of the present invention are intended to be illustrative only and are not to be construed as limiting.

EXAMPLE 1

Room temperature polymerizing resin systems were prepared. These systems comprised powdered poly (ethylmethacrylate) containing 0.6% by weight benzoyl peroxide as a polymerization initiator and liquid tetrahydrofurfuryl methacrylate containing 2.5% v/v of N,N'-dimethyl-p-toluidine as an activator. The polymer/monomer ratio was 1.0 g/0.6 ml or appropriate multiples thereof. The samples contained 0%, 0.5% or 1% w/w sodium fluoride having an average particle size of 400 micrometers.

Figure 2:
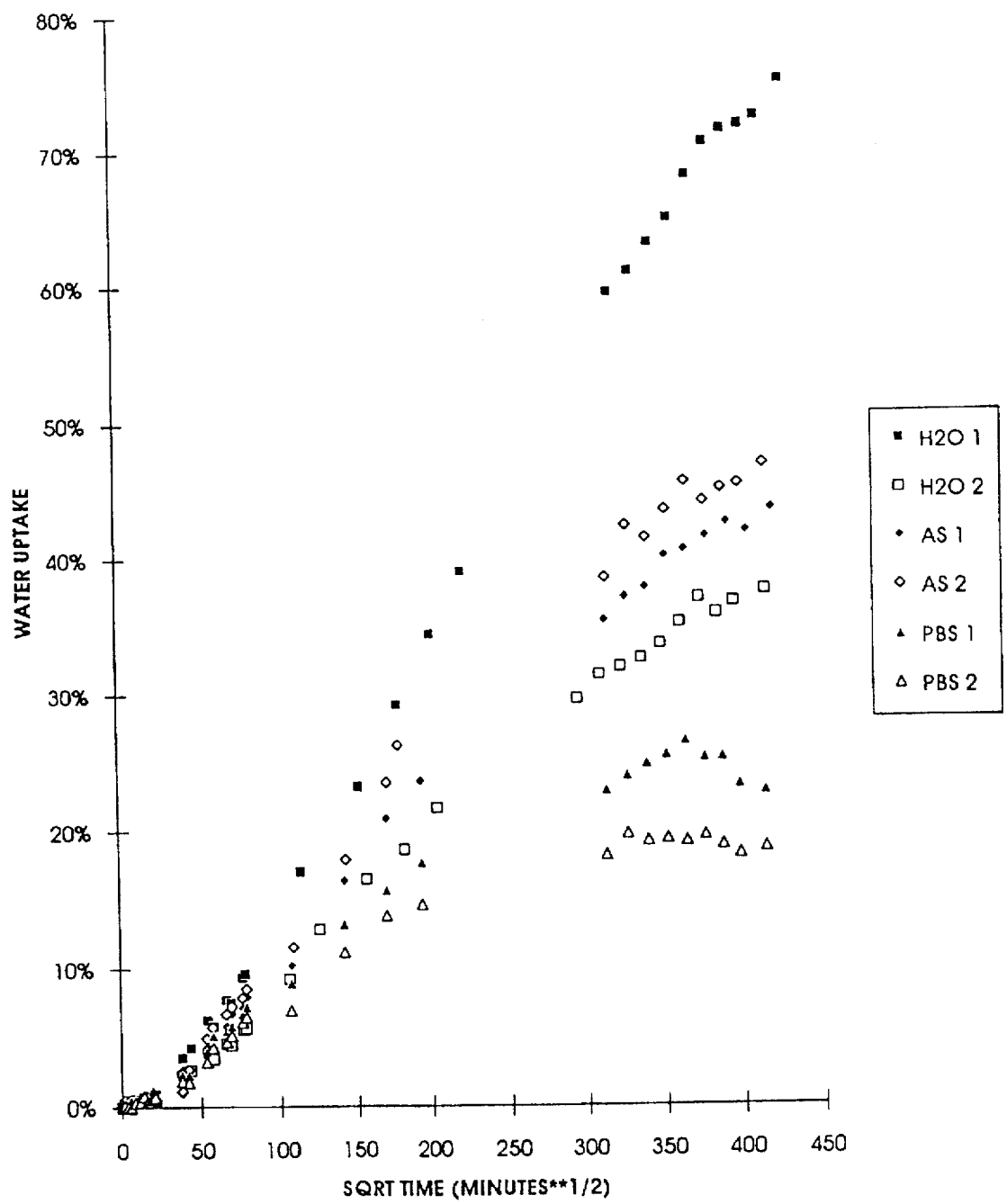
FIG. 2 illustrates the water uptake of the composition of Example 1 containing 0.5% w/w sodium fluoride in various media.
Figure 3:
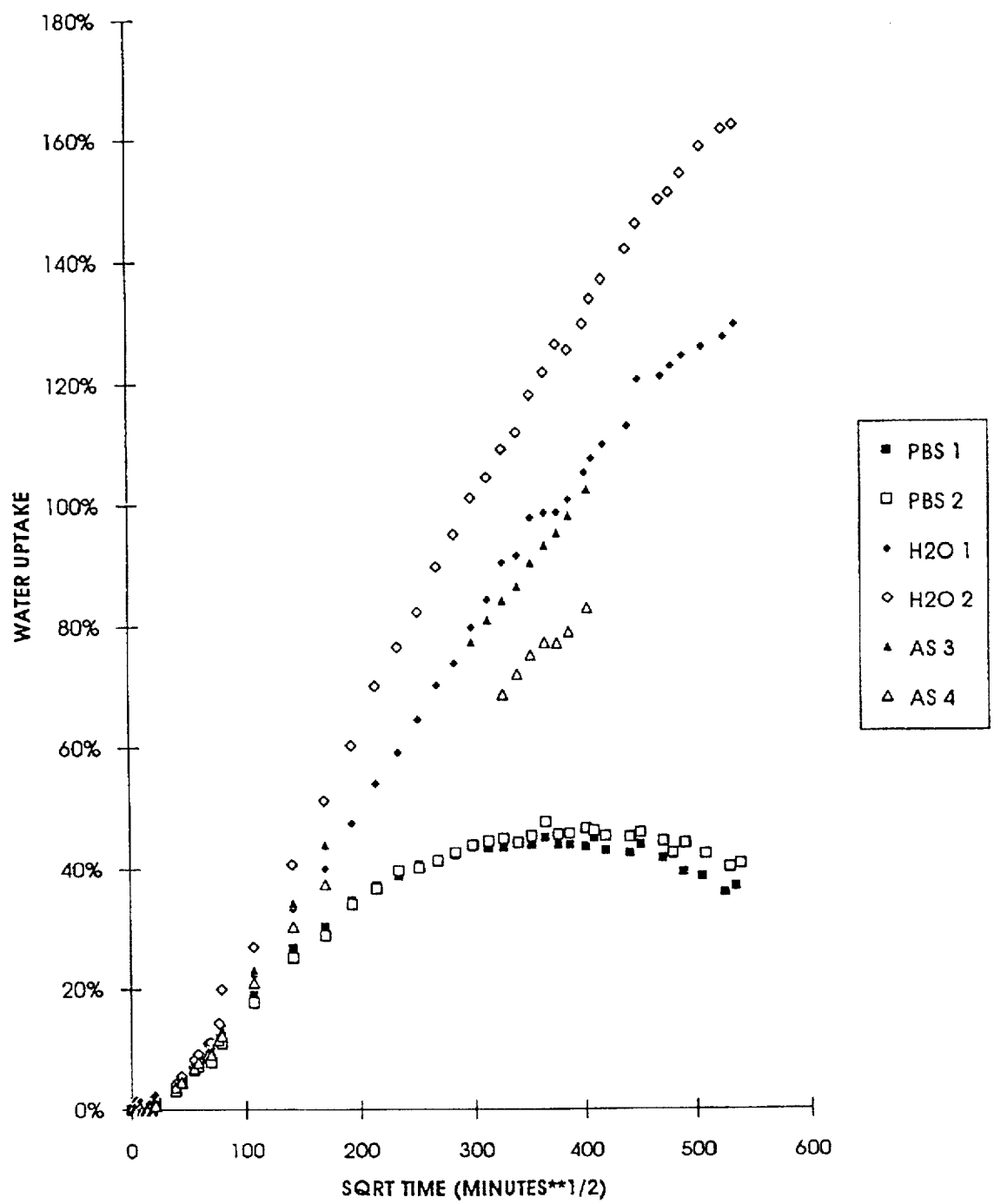
FIG. 3 illustrates the water uptake of the composition of Example 1 containing 1% w/w sodium fluoride in various media.

The samples were prepared in the form of discs. Each disc had a diameter of 15 mm and was 1 mm deep. The samples were pre-weighed and immersed in distilled water, artificial saliva or phosphate buffered saline. The water uptake for the compositions containing 0%, 0.5% and 1% w/w sodium fluoride in distilled water, artificial saliva or phosphate buffered saline are shown in FIGS. 1, 2 and 3.

Figure 4:
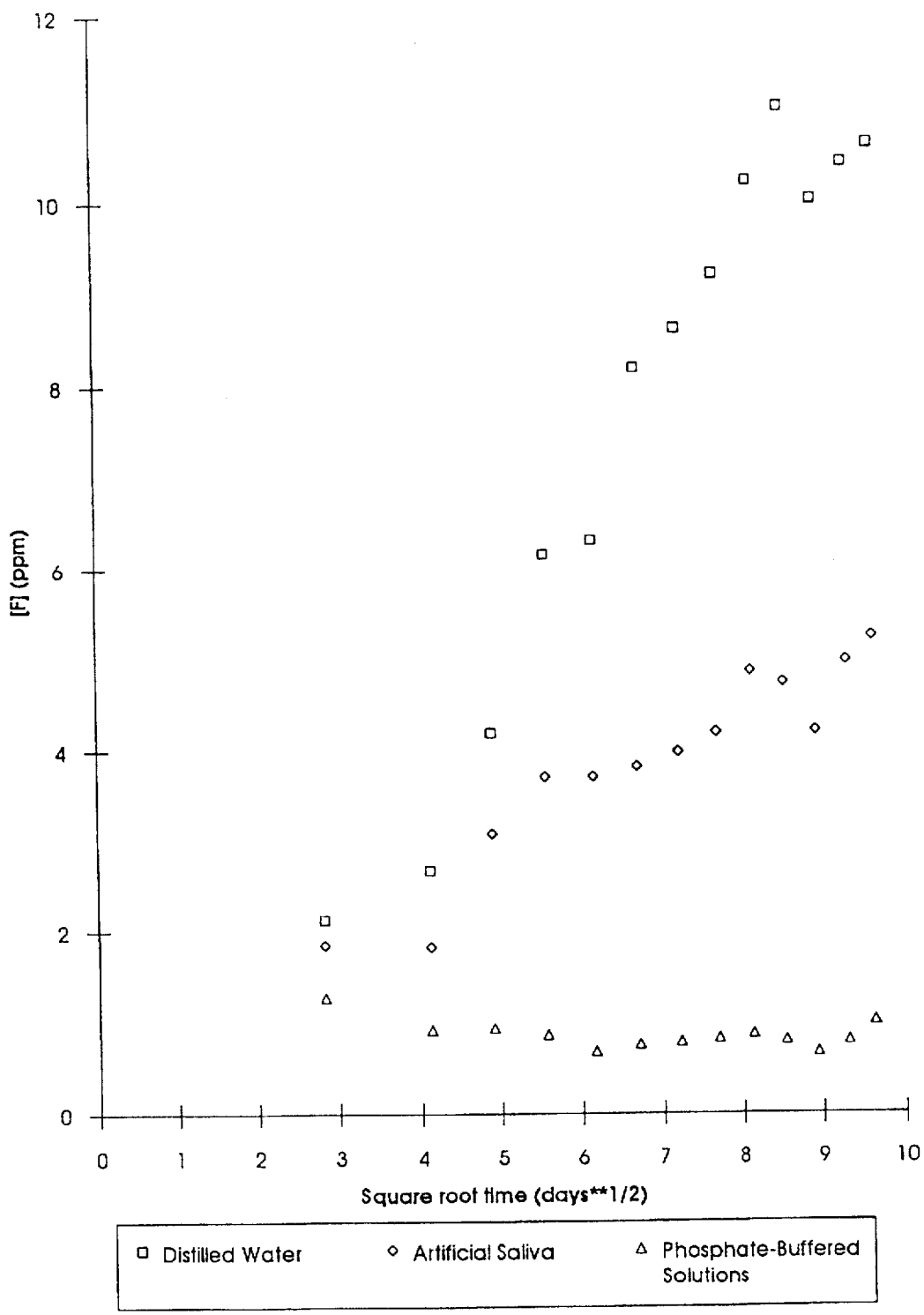
FIG. 4 illustrates fluoride release from the composition of Example 1 containing 1% w/w sodium fluoride in various media.

The fluoride released from the sample containing 1% w/w sodium fluoride in distilled water, artificial saliva or phosphate buffered saline was determined by the method of Tyler, J. E. and Poole, D. F. G. Arch. Oral Biol. 1989, 34, pages 995 to 998. The results are shown in FIG. 4.

EXAMPLE 2

A The procedure of Example 1 was repeated but using sodium fluoride having a particle size of 50 to 100 μm obtained by grinding and sieving sodium fluoride powder.

B The procedure of Example 1 was repeated replacing tetrahydrofurfuryl methacrylate with n-butyl methacrylate and using sodium fluoride having a particle size of 50 to 150 μm obtained by grinding and sieving sodium fluoride powder.

The Table below gives the release data after 18 weeks for the samples from experiments A and B above immersed in water, artificial saliva and phosphate buffered saline.

TABLE

| RELEASE OF FLUORIDE (parts per million) | | | | |
|---|---|---|---|---|
| | A | | B | |
| % NaF | 0.5 | 1.0 | 0.5 | 1.0 |
| $H_2O$ | 1.5 | 1.8 | 1.0 | 2.1 |
| Artificial Saliva | 1.0 | 1.3 | 0.9 | 1.9 |
| Phosphate Buffered Saline | 1.3 | 1.7 | 1.1 | 1.9 |

Having thus described some embodiments of the present invention, various alterations, modifications and improvements will readily occur to those skilled in the art. Such alterations, modifications and improvements are intended to be part of this disclosure and are intended to be within the spirit and scope of the invention. Accordingly, the foregoing is by way of example only and is not intended as limiting. The invention is limited only as defined in the following claims and the equivalents thereto.

What is claimed is:

1. A fluoride releasing dental composition, comprising:
   a polymer selected from the group consisting of methacrylate polymers, methacrylate copolymers, and mixtures thereof;
   a monomer selected from the group consisting of monomeric heterocyclic methacrylic esters, $C_3$–$C_4$ methacrylic esters, and mixtures thereof; and
   a non-toxic, biologically acceptable metal fluoride, wherein the dental composition comprises from approximately 0.5% to approximately 2% metal fluoride by weight, and wherein the ratio of the polymer to the monomer is from 1.25:1 to 1.75:1 by weight.

2. The fluoride releasing dental composition according to claim 1, wherein the monomer is tetrahydrofurfuryl methacrylate.

3. The fluoride releasing dental composition according to claim 1, wherein the monomer is a monomeric heterocyclic methacrylic ester, the monomer having a molecular formula of

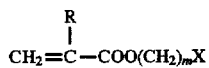

wherein R is a methyl group, m is selected from the group consisting of 0, 1 and 2, and X comprises a heterocyclic ring having from 3 to 6 members.

4. The fluoride releasing dental composition according to claim 3, wherein the heterocyclic ring includes an oxygen atom.

5. The fluoride releasing dental composition according to claim 1, wherein the monomer is a butyl methacrylate.

6. The fluoride releasing dental composition according to claim 1, wherein the polymer is a polyalkylmethacrylate.

7. The fluoride releasing dental composition according to claim 1, wherein the polymer is a polyethylmethacrylate.

8. The fluoride releasing dental composition according to claim 1, wherein the metal fluoride is sodium fluoride.

9. The fluoride releasing dental composition according to claim 1, further comprising at least one filler material.

10. The fluoride releasing dental composition according to claim 1, wherein the composition is a dental coating material, a dental filling material, an endodontic material or orthodontic material.

11. The fluoride releasing dental composition according to claim 1, wherein the dental composition comprises from approximately 0.5% to approximately 1% metal fluoride by weight.

* * * * *